(12) United States Patent
Wang et al.

(10) Patent No.: US 7,071,000 B2
(45) Date of Patent: Jul. 4, 2006

(54) METHOD FOR SAMPLING REACTION PRODUCTS

(75) Inventors: Youqi Wang, Atherton, CA (US); Peijun Cong, San Jose, CA (US); Tony N. Wheeler, Santa Clara, CA (US); Lynn Thomas Van Erden, Livermore, CA (US); H. Sam Bergh, San Francisco, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 480 days.

(21) Appl. No.: 10/334,099

(22) Filed: Dec. 30, 2002

(65) Prior Publication Data

US 2003/0100120 A1  May 29, 2003

Related U.S. Application Data

(62) Division of application No. 09/652,489, filed on Aug. 31, 2000, now Pat. No. 6,864,091.

(51) Int. Cl.
*G01N 31/10* (2006.01)
*G01N 1/22* (2006.01)
*G01N 35/10* (2006.01)
*H01J 49/00* (2006.01)

(52) U.S. Cl. .................. 436/37; 73/863.83; 73/863.84; 73/864; 73/864.11; 73/864.21; 73/864.35; 73/864.62; 73/864.72; 73/864.83; 73/864.84; 73/864.85; 250/288; 436/43; 436/173; 436/181

(58) Field of Classification Search ............ 73/863.32, 73/863.52, 863.83–863.84, 864, 864.01, 73/864.11, 864.14, 864.21, 864.35, 864.62, 73/864.72–864.73, 864.83–864.85; 141/130; 210/198.2; 250/281–282, 288; 422/63–67, 422/100, 103; 436/20–30, 37, 43, 173, 180–181
See application file for complete search history.

(56) References Cited

U.S. PATENT DOCUMENTS

| 3,596,087 A | 7/1971 | Heath |
| 3,607,094 A | 9/1971 | Beer |
| 3,610,048 A | 10/1971 | Weeks |
| 3,699,348 A * | 10/1972 | Hocherl ..................... 250/576 |
| 3,842,266 A | 10/1974 | Thomas |
| 3,944,826 A | 3/1976 | Gray |
| 4,099,923 A | 7/1978 | Milberger |
| 4,213,326 A | 7/1980 | Brodasky |
| 4,368,080 A | 1/1983 | Langen et al. |
| 4,408,125 A | 10/1983 | Meuzelaar |

(Continued)

FOREIGN PATENT DOCUMENTS

DE   43 21 062 A1   1/1995

(Continued)

OTHER PUBLICATIONS

Rogers, D. E. et al, Applied Catalysis 1989, 51, 181-194.*

(Continued)

*Primary Examiner*—Arlen Soderquist
(74) *Attorney, Agent, or Firm*—Senniger Powers

(57) ABSTRACT

A method for sampling reaction products includes delivering a reactant through a sampling probe to contact a substance deposited on a substrate and reacting the reactant to form a reaction product. At least a portion of the reaction product is withdrawn through the sampling probe and analyzed. The sampling probe is contacted with the substrate during at least a portion of the delivering, reacting and withdrawing steps.

7 Claims, 6 Drawing Sheets

U.S. PATENT DOCUMENTS

| | | |
|---|---|---|
| 4,489,590 A | 12/1984 | Hadden |
| 4,626,412 A | 12/1986 | Ebner et al. |
| 4,705,616 A | 11/1987 | Andresen et al. |
| 4,791,292 A | 12/1988 | Cooks et al. |
| 4,803,050 A | 2/1989 | Mack |
| 4,852,620 A | 8/1989 | Jakubowicz et al. |
| 4,877,584 A | 10/1989 | Yates, Jr. et al. |
| 4,879,242 A | 11/1989 | Tsukioka |
| 4,988,626 A | 1/1991 | Ajot et al. |
| 5,009,849 A | 4/1991 | Ebner et al. |
| 5,077,470 A | 12/1991 | Cody et al. |
| 5,146,088 A | 9/1992 | Kingham et al. |
| 5,191,211 A | 3/1993 | Gorman, Jr. |
| 5,439,830 A | 8/1995 | Sakashita et al. |
| 5,926,273 A | 7/1999 | Kimura et al. |
| 5,959,297 A | 9/1999 | Weinberg et al. |
| 6,066,848 A | 5/2000 | Kassel et al. |
| 6,087,181 A | 7/2000 | Cong |
| 6,309,541 B1 | 10/2001 | Maiefski et al. |
| 6,355,164 B1 | 3/2002 | Wendell et al. |
| 6,358,414 B1 | 3/2002 | Maiefski |
| 6,569,687 B1 | 5/2003 | Doktycz et al. |
| 6,864,091 B1 * | 3/2005 | Wang et al. ............... 436/37 |

FOREIGN PATENT DOCUMENTS

| | | |
|---|---|---|
| EP | 0 260 469 A2 | 3/1988 |
| EP | 0 371 572 A2 | 6/1990 |
| EP | 0 408 487 A2 | 1/1991 |
| EP | 1 019 947 B1 | 8/2002 |
| WO | WO 81/03394 A1 | 11/1981 |
| WO | WO 95/25737 A1 | 9/1995 |
| WO | WO 96/11878 A1 | 4/1996 |
| WO | WO 96/22530 A1 | 7/1996 |
| WO | WO 97/32208 A1 | 9/1997 |
| WO | WO 98/03521 | 1/1998 |
| WO | WO 98/07026 A1 | 2/1998 |
| WO | WO 98/16949 A1 | 4/1998 |
| WO | WO 00/29844 A1 | 5/2000 |
| WO | WO 00/65326 | 11/2000 |

OTHER PUBLICATIONS

Lavalley, J. C. et al., SPIE 1990, 1341, 244-255.*

Maciejewski, M. et al, Thermochimica Acta 1997, 295, 167-182.*

Puxley, D. C. et al, Journal of Applied Crystallography 1994, 27, 585-594.*

Kopac, T. et al, Chemical Engineering Science 1996, 51), 2201-2209.*

Zech, T. et al, Microreaction Technology: Industrial Prospects, Proceedings of the International Conference on Microreaction Technology, 3rd, Frankfurt, Apr. 18-21, 1999, 260-266, Editor: Ehrfeld, Wolfgang, Publisher: Springer-Verlag, Berlin, Germany.*

Balzers, MS-Cube™ Specification Sheets, 1993.

Singoredjo, L., et al., "Selective Catalytic Reduction of NO with $NH_3$ Over Carbon Supported Copper Catalysts", *Catalysis Today*, 1990, pp. 157-165, Elsevier Science Publishers B.V., Amsterdam, The Netherlands.

Huang, Y, et al., "Collision-Induced Dissociation for Mass Spectrometric Analysis of Biopolymers: High-Resolution Fourier Transform Ion Cyclotron Resonance $MS^4$", *Analytical Chemistry*, Dec. 15, 1994, pp. 4385-4389, vol. 66, No. 24, Washington, DC.

Kelly, M.A., et al., "Characterization of SH2-Ligand Interactions via Library Affinity Selection with Mass Spectrometric Detection", Biochemistry, 1996, pp. 11747-11755, vol. 35, No. 36, American Chemical Society.

M. Kiskinova, G.L. Griffin, and J.T. Yates, Jr., "Thermal Desorption Spectroscopy from High-Specific-Area Solids—Hydrocarbon Adsorption and Diffusion in NaX Zeolite Crystals", 71 *Journal of Catalysis* 278-287 (1981).

Cong, Peijun, et al., High-Throughput Synthesis and Screening of Combinatorial Heterogeneous Catalyst Libraries, *Communications*, Agnew. Chem. Int. Ed., Feb. 15, 1999, pp. 483-488, vol. 38, No. 4, WILEY-VCH Verlag GmbH, Weinheim.

* cited by examiner

METHOD FOR SAMPLING REACTION PRODUCTS

CROSS-REFERENCE TO RELATED APPLICATIONS

This application is a divisional of co-pending U.S. patent application Ser. No. 09/652,489 filed Aug. 31, 2000, which issued on Mar. 8, 2005, as U.S. Pat. No. 6,864,091, the entire text of which is incorporated herein by reference.

BACKGROUND OF THE INVENTION

The present invention relates generally to probes for reaction product analyzers such as scanning mass spectrometers and photothermal deflection spectrometers, and more particularly to a sampling probe for delivering reactants to substances such as catalysts and for sampling resulting reaction products.

Various conventional reaction product analyzers are used for analyzing characteristics of reaction products formed by reacting reactants. One such analyzer is a mass spectrometer. One type of spectrometer known as a scanning mass spectrometer may be used to identify the particles present in each reaction product in an array of reaction products. This type of spectrometer has a probe which delivers reactants to each substance (e.g., a catalyst) in an array of substances. The reactants are allowed to react to form reaction products and the probe draws a portion of each reaction product into an ionization chamber of the scanning mass spectrometer for analysis. Using scanning mass spectrometers, hundreds of reaction products can be analyzed over a relatively short period of time. Such scanning mass spectrometers and methods for their use are further described in U.S. Pat. No. 5,959,297, issued Sep. 29, 1999, entitled, "Mass Spectrometers and Methods for Rapid Screening of Libraries of Different Materials", which is hereby incorporated by reference.

A photothermal deflection spectrometer is another type of reaction product analyzer used to analyze characteristics of reaction products. In photothermal spectrometers, a sample (e.g., a reaction product) is excited with optical radiation from a source such as an infrared laser. The sample absorbs some of the radiation resulting in a change in the sample temperature and density which affect other properties of the sample. Photothermal spectrometers measure the changes in the refractive index of the sample resulting from exciting it with radiation. One such photothermal spectrometer is described in U.S. Pat. No. 6,087,181, issued Jul. 11, 2000, entitled, "Sampling and Detection of Trace Gas Species by Optical Spectrography", which is hereby incorporated by reference.

Conventional sampling probes used with product analyzers have a recessed tip which is positioned over each substance in an array of substances deposited on a substrate for delivering the reactant and drawing the reaction product. Although the tip does not touch the substrate which holds the substances, it is positioned near the substrate (e.g., within about 100 micrometers) to hold the reactants and reaction products in the recess and to physically prevent them from contaminating adjacent substances in the array. The longer the period of time the reactants are held in the recess, the longer they can react. When a gap is left between the tip and the substrate, the reaction time is generally determined by the diffusion time of the reactants from the center of the recess to its edge. A conventional scanning mass spectrometer probe has a relatively short reaction time, typically on the order of 1 millisecond to about 10 milliseconds.

Due to the inherent limitations of conventional sampling probes, reaction products from low activity reactants are difficult to detect, particularly where relatively long reaction times are required. Further, the conventional sampling probes do not entirely eliminate the potential for contamination of adjacent substances on the substrate.

SUMMARY OF THE INVENTION

Among the several objects and features of the present invention may be noted the provision of a sampling probe which significantly increases the contact time or residence time between the reactants and the substances; the provision of a sampling probe which significantly reduces the potential of contaminating adjacent substances on a substrate; and the provision of a probe which is capable of detecting reaction products from low activity reactants.

Briefly, apparatus of this invention is a sampling probe for delivering a reactant to a substance deposited on a substrate to form a reaction product and for transporting the reaction product to a product analyzer for analysis. The probe includes a tip positionable over the substance on the substrate. The probe has a recess in the tip sized and shaped for receiving at least a portion of the reaction product. The probe has a product sampling passage extending from the recess adapted for connection to the product analyzer for transporting at least the portion of the reaction product to the product analyzer. Further, the probe has a reactant delivery passage extending to an outlet positioned outside the recess for delivering reactant to the substance on the substrate to form the reaction product.

In another aspect of the invention, the probe includes a barrier surrounding the area outside the recess for reducing emission of reaction products beyond the barrier.

In yet another aspect of the present invention, the probe comprises an inner body and an outer body having an inner cavity sized and shaped for receiving the inner body. The inner body includes a tip for engaging the substrate and has a recess sized and shaped for receiving at least a portion of the reaction product. The probe also includes a reactant delivery passage and a product sampling passage.

In still another aspect of the present invention, the probe comprises a tip, a mixing chamber positioned inside the probe for mixing reactants therein, and a plurality of reactant source passages extending through the probe from a plurality of reactant sources to the mixing chamber. A reactant delivery passage extends from the mixing chamber to an outlet positioned at the tip for delivering reactants to the substance on the substrate.

In another aspect of the present invention, the probe comprises a body, a tip, a resiliently compliant element positioned between the tip and the body for permitting the tip to move relative to the body, a recess in the tip, a product sampling passage, a vent passage and a reactant delivery passage.

The present invention also includes a method for sampling reaction products. The method includes delivering a reactant through a sampling probe to contact a substance deposited on a substrate and reacting the reactant to form a reaction product. At least a portion of the reaction product is withdrawn through the sampling probe and analyzed. The sampling probe is contacted with the substrate during at least a portion of the delivering, reacting and withdrawing steps.

In another aspect of the invention, a method of present invention includes delivering a reactant through a sampling probe to contact a substance deposited on a substrate and reacting the reactant to form a reaction product. The reactant has a contact time of greater than 1 second. The method also includes the steps of withdrawing at least a portion of the reaction product through the sampling probe and analyzing the withdrawn portion of the reaction product.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
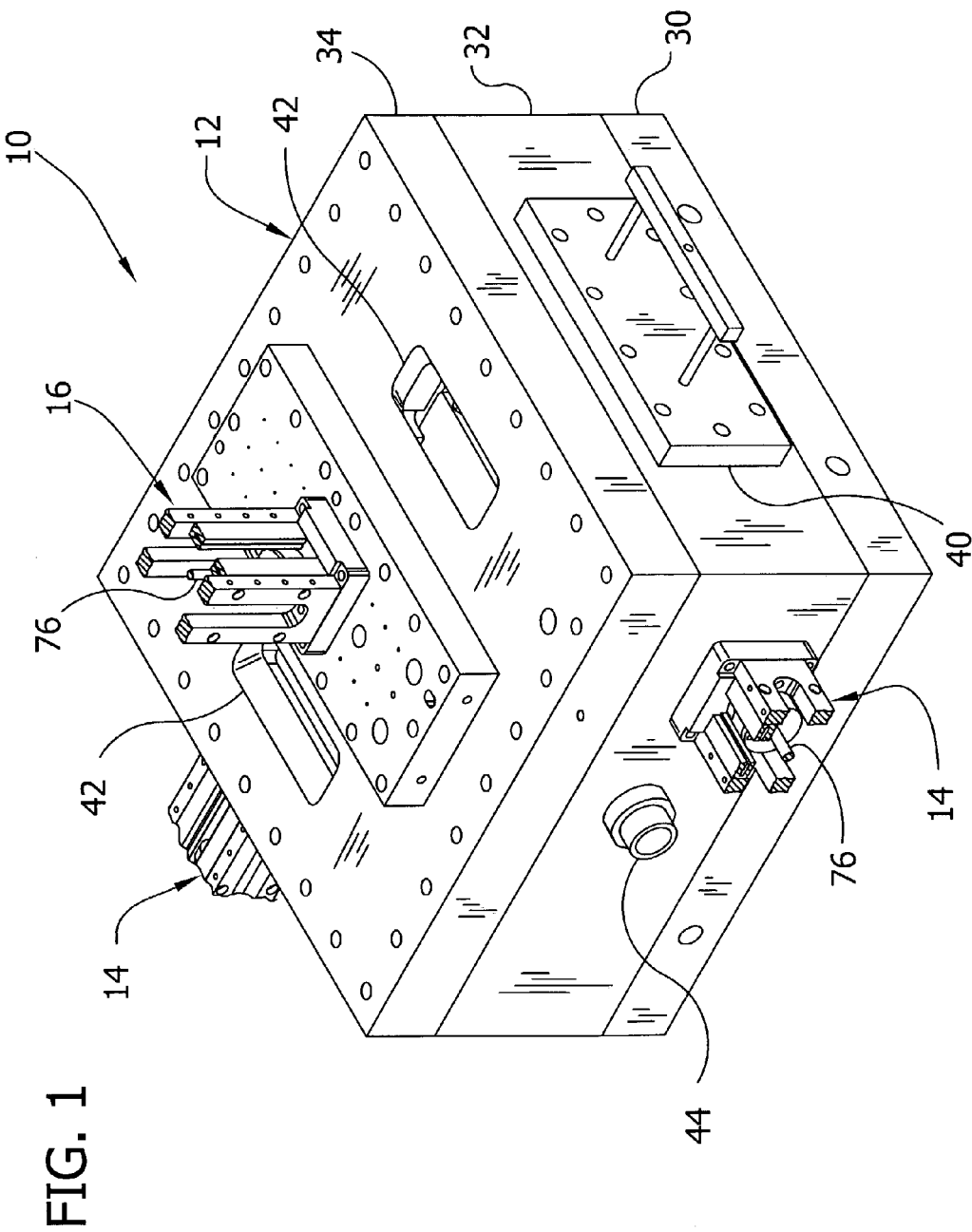
FIG. 1 is a fragmentary isometric view of a reaction chamber of the present invention.
Figure 2:
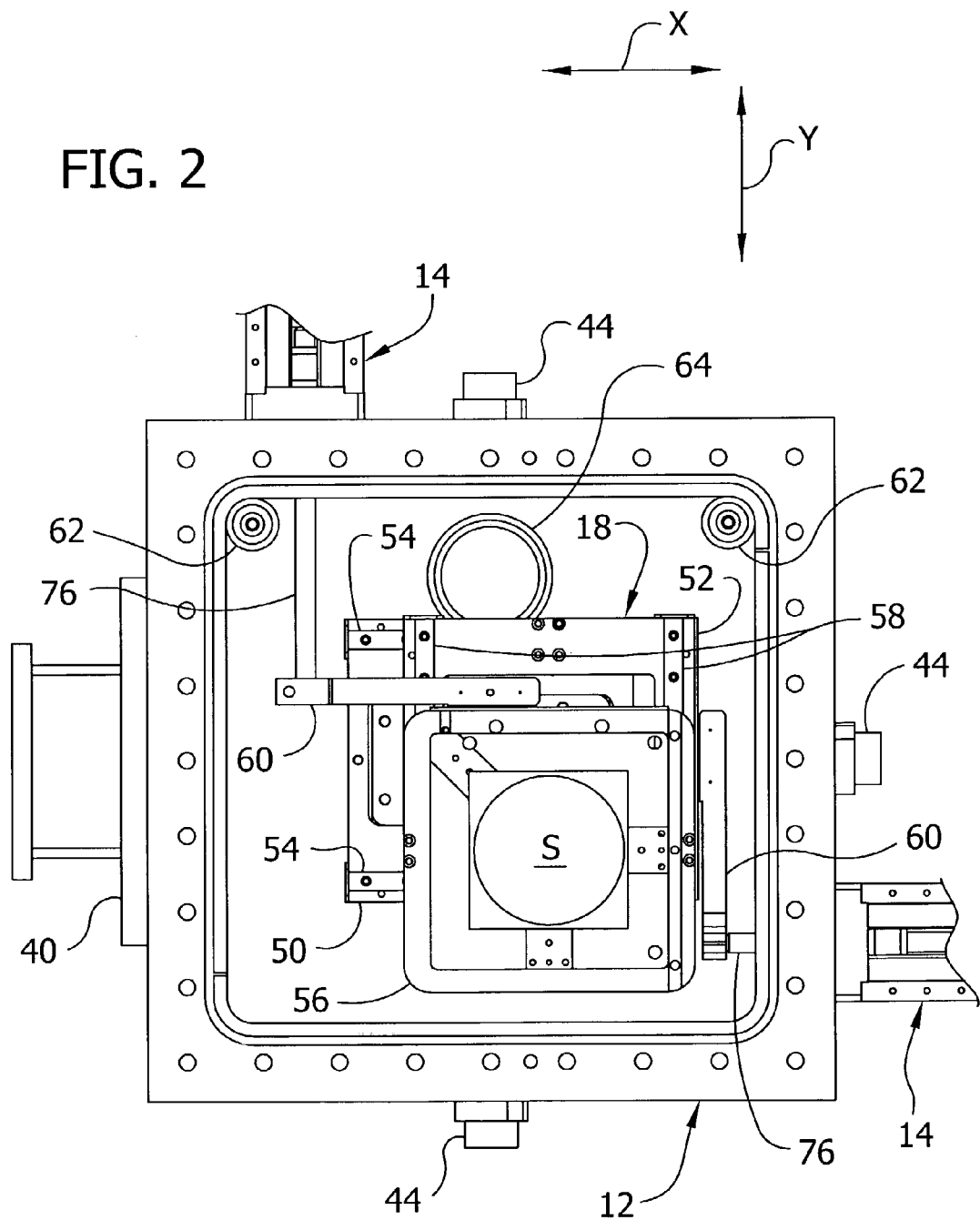
FIG. 2 is a fragmentary top plan of the chamber having a top panel removed.
Figure 3:
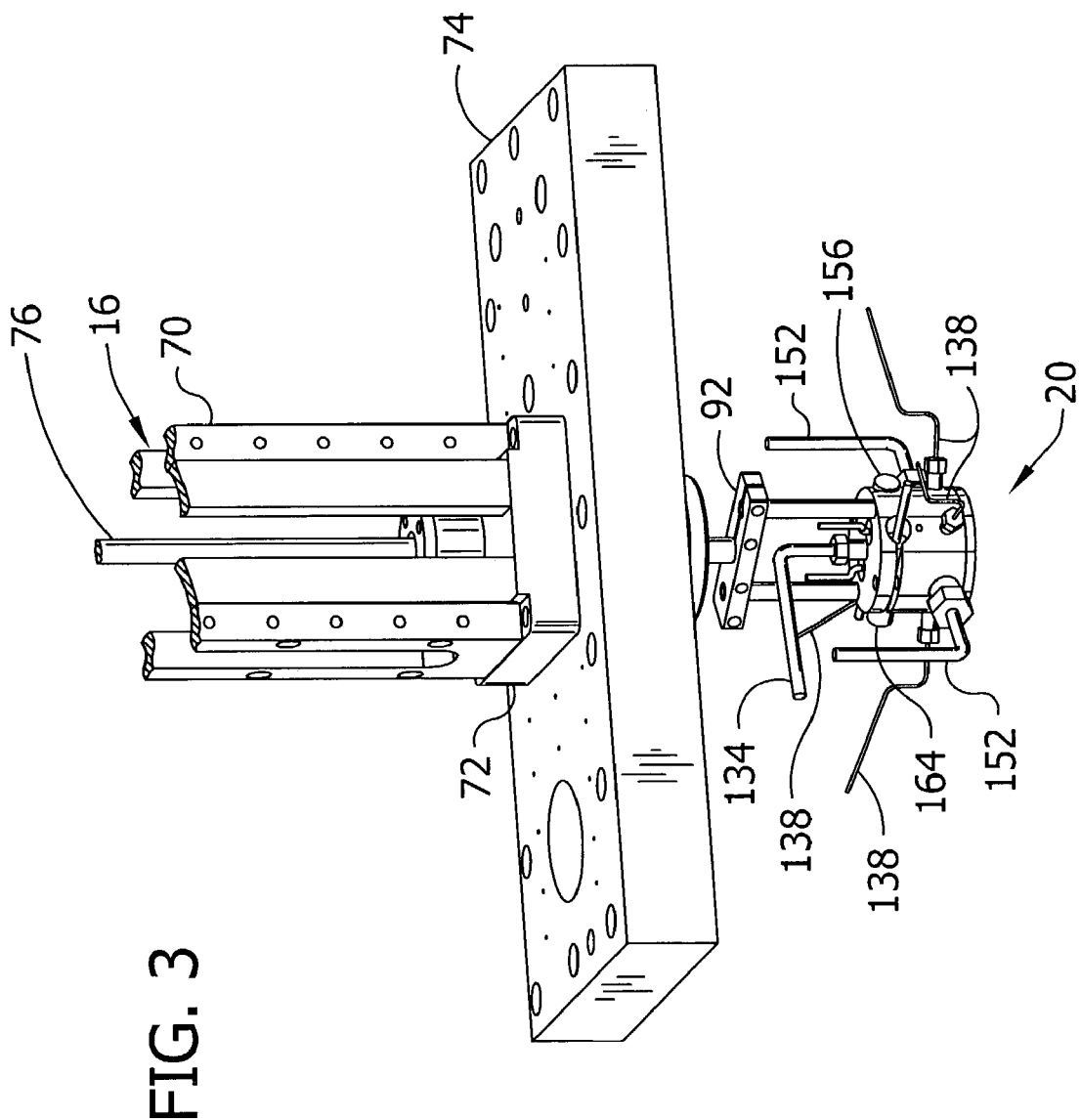
FIG. 3 is a fragmentary isometric view of a probe of the present invention.

Referring now to the drawings and in particular to FIG. 1, a portion of a scanning mass spectrometer, more particularly a scanning mass spectrometer reaction chamber, is designated in its entirety by the reference numeral 10. The reaction chamber 10 comprises an enclosure, generally designated by 12, having two horizontally-oriented, feedthrough actuator assemblies, generally designated by 14, and one vertically-oriented, feedthrough actuator assembly, generally designated by 16. As shown in FIG. 2, the horizontally-oriented actuator assemblies 14 are connected to a stage, generally designated by 18, mounted inside the enclosure 12 for supporting a substrate S. As illustrated in FIG. 3, the vertically-oriented actuator assembly 16 is connected to a probe, generally designated by 20, for delivering reactants to substances M (FIG. 4) deposited on the substrate S to form reaction products and for withdrawing a portion of each reaction product for analysis as will be explained in greater detail below.

As further illustrated in FIG. 1, the enclosure 12 includes a bottom 30, a middle section 32 and a top 34. Threaded fasteners (not shown) are used to fasten the bottom 30, middle section 32 and top 34 together. A removable panel 40 is attached to the middle section 32 for covering an opening (not shown) in the middle section through which the substrate S is loaded and unloaded. Windows 42, 44 are provided in the top 34 and the middle section 32, respectively, for viewing an interior of the enclosure 12.

As illustrated in FIG. 2, the stage 18 includes a base 50 mounted on the bottom 30 of the enclosure 12, a first element 52 slidably mounted on the base with a first pair of linear bearings 54, and a second element 56 slidably mounted on the first element with a second pair of linear bearings 58. The first pair of linear bearings 54 permit the first element 52 to slide horizontally in a first direction X with respect to the base 50. The second pair of linear bearings 58 permit the second element 56 to slide horizontally in a second direction Y with respect to the first element 52. One of the horizontally-oriented actuator assemblies 14 is attached to the first element 52 and one is attached to the second element 56 to selectively align the probe 20 (FIG. 3) with each of the substances M deposited on the substrate S. An arm 60 extends laterally from each horizontally-oriented actuator assembly 14 for connecting the respective assembly to the stage 18. Each arm 60 includes magnets (not shown) for attaching the respective arm to the stage 18. A roller (not shown) is provided on the arm 60 attached to the second element 56 to permit the arm to move laterally with respect to the stage 18. Because the stage 18 is conventional, it will not be described in further detail. Conventional pneumatic fittings 62 extend through the bottom 30 for connecting the enclosure 12 to a source of pressurized inert gas (not shown) for pressurizing the interior of the enclosure. A larger fitting 64 extends through the bottom 30 for connecting the enclosure 12 to a vacuum source (not shown) to evacuate the enclosure. It is envisioned that the stage 18 and/or enclosure 12 may include a conventional heating element to heat the substances M deposited on the substrate S to enhance the reaction.

Each of the horizontally-oriented and vertically-oriented actuator assemblies 14, 16, respectively, is substantially identical. Thus, for brevity only the vertically-oriented actuator assembly 16 shown in FIG. 3 will be described in further detail. The assembly 16 generally includes a frame 70 which is attached to the enclosure 12 at a first end 72. In contrast to the horizontal assemblies 14, the vertically-oriented actuator assembly 16 includes a mounting plate 74 at the first end 72 for attaching the frame 70 to the enclosure 12. A conventional rotary actuator (not shown) is mounted on a second end (not shown) of the frame 70 opposite the first end 72. The rotary actuator drives a threaded drive rod assembly 76 toward and away from the enclosure 12 as the actuator rotates. As will be appreciated by those skilled in the art, the rotary actuator may be a conventional pneumatic or a conventional electric actuator. The drive rod assembly 76 extends into the enclosure 12. In the case of the horizontally-oriented actuator assemblies 14, the previously described arm 60 is mounted on an end of the drive rod assembly 76 positioned inside the enclosure 12. In the case of the vertically-oriented actuator assembly 16, a mounting bracket 92 is attached to the end of the drive rod assembly 76 positioned inside the enclosure 12. The probe 20 is mounted on the mounting bracket 92.

Figure 4:
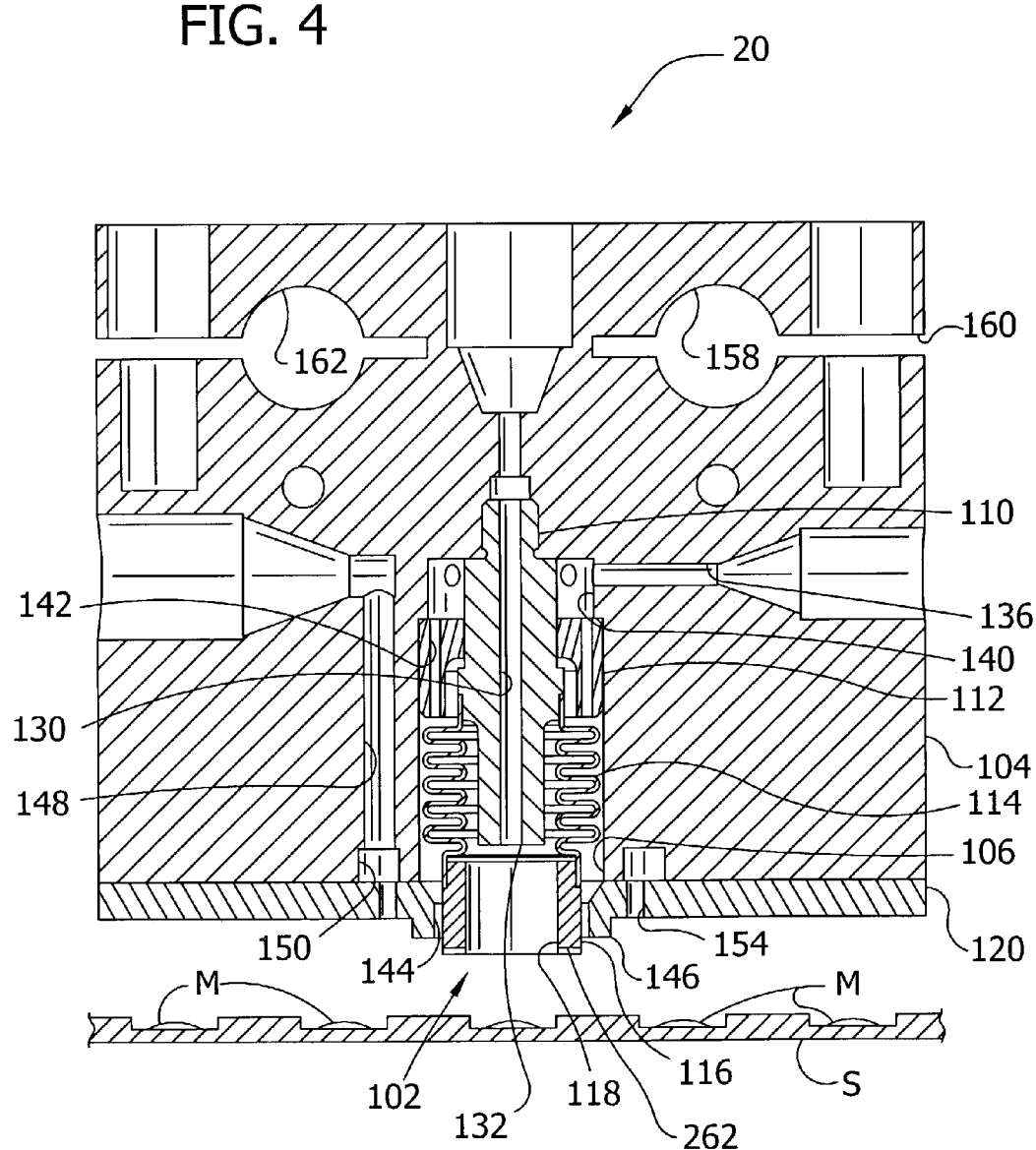
FIG. 4 is a vertical cross section of a first embodiment of the probe of the present invention.

As illustrated in FIG. 4, the probe 20 includes an inner body, generally designated by 102, and an outer body 104 having an inner cavity 106 sized and shaped for receiving the inner body. The inner body 102 includes a threaded fitting 110, a collar 112 surrounding the fitting, a resiliently compliant element 114 attached to the fitting 110 inside the collar, and a cylindrical tip 116 attached to the lower end of the compliant element for engaging the substrate S as will be explained in greater detail below. The tip 116 has a hollow interior forming a recess 118 sized and shaped for receiving at least a portion of the substance M when the tip 116 engages the substrate S. Although other compliant elements such as a diaphragm or spring may be used without departing from the scope of the present invention, in one embodiment the compliant element is a bellows. The compliant element 114 allows the tip 116 to tilt when seating against the substrate S to account for small amounts of non-parallelism between the tip and the substrate. Thus, the tip 116 is adapted to engage the substrate S entirely around the recess 118. As will be appreciated by those skilled in the art, the collar 112 centers the fitting 110, bellows 114 and tip 116 in the cavity 106 of the outer body 104. A cover 120 is attached to the lower end of the outer body 104. Although the cover 120 may be attached by other means without departing from the scope of the present invention, in one embodiment the cover is attached by screw fasteners (not shown).

The probe 20 includes a product sampling passage 130 extending upward from an inlet 132 in the recess 118 through the threaded fitting 110 and outer body 104 to a tube 134 (FIG. 3) connected to an ionization chamber (not shown) of a conventional scanning mass spectrometer (not shown) or to some other product analyzer. The tube 134 transports at least a portion of a reaction product from the product sampling passage 130 to the ionization chamber. The probe 20 also includes reactant source passages 136 extending through the outer body 104 from tubes 138 (FIG. 3) connected to a plurality of reactant sources (e.g., four separate sources, not shown). Although the probe 20 may be connected to fewer or more tubes 138 without departing from the scope of the present invention, in one embodiment the probe is connected to four tubes. The reactant source passages 136 extend to a mixing chamber 140 defined in part by the inner cavity 106 of the outer body 104 where reactants traveling through the tubes 138 from different reactant sources mix before traveling to the substances M deposited on the substrate S. The reactant exits the mixing chamber 140 through a plurality of reactant delivery passages 142 in the collar 112 and then flows between an exterior surface of the inner body 102 and an interior surface of the cavity 106 to an outlet defined by an exterior surface of the tip 116 and an opening 144 in the cover 120 to contact the substance M deposited on the substrate S immediately below the tip 116. As will be appreciated by those skilled in the art, the reactant reacts to form a reaction product which is analyzed by the scanning mass spectrometer. The tip 116 surrounding the recess 118 forms a barrier for containing reactants and reaction products in the recess. A second barrier 146 extending downward from the cover 120 surrounds the opening 144 and the recessed tip 116.

To prevent reactant from contaminating adjacent substances M deposited on the substrate S, a vent passage 148 is provided in the probe 20. The vent passage 148 extends from an annular cavity 150 surrounding the cavity 106 of the outer body 104 to tubes 152 (FIG. 3) connected to a facility exhaust system (not shown). A series of holes 154 provided in the cover 120 form inlets for permitting the reactants and reaction products to pass through the cover 120 and enter the cavity 150 and vent passage 148.

Conventional instrumentation is also provided on the probe 20. For instance, a heater 156 (FIG. 3) is positioned in an opening 158 in the outer body 104. The opening 158 includes a slot 160 which may be compressed to clamp the heater in the opening. A similar opening 162 is provided for holding a temperature sensor 164 (FIG. 3) in the probe 20.

Figure 5:
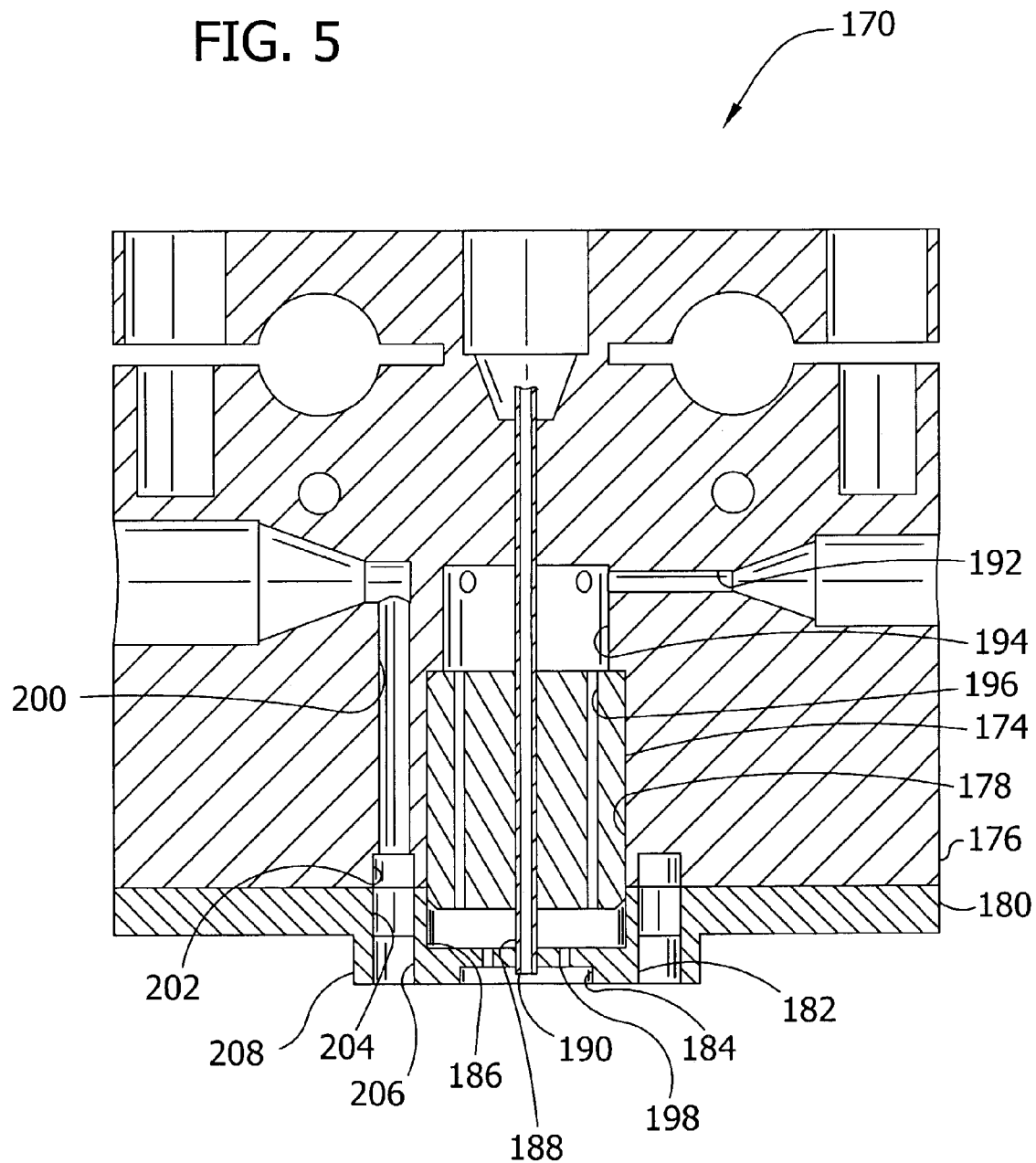
FIG. 5 is a vertical cross section of a second embodiment of the probe of the present invention.

As will be appreciated by those skilled in the art, the probe may have other embodiments without departing from the scope of the present invention. As illustrated in FIG. 5, a probe 170 of a second embodiment includes an inner body or plug 174 and an outer body 176 having an inner cavity 178 sized and shaped for receiving the inner body. A cover 180 is attached to a lower end of the outer body 176 for capturing the inner body 174 in the inner cavity 178. The cover 180 includes a central tip 182 having a recess 184 sized and shaped for receiving at least a portion of the substance M (FIG. 4). The cover 180 also includes a recess 186 in its upper face sized and shaped for receiving a lower end of the inner body 174. A tube 188 extends upward from an inlet 190 in the lower recess 184 through the cover 180, inner body 174 and outer body 176 to form a product sampling passage which communicates with the tube 134 (FIG. 3) connected to the ionization chamber of the spectrometer to transport reaction products to the chamber for analysis.

The probe 170 also includes reactant source passages 192 extending through the outer body 176 from the tubes 138 (FIG. 3) connected to reactant sources (not shown). The reactant source passages 192 extend to a mixing chamber 194 defined in part by the inner cavity 178 of the outer body 176 where reactants mix before traveling through reactant delivery passages 196 extending through the inner body 174 to the upper recess 186 in the cover which forms a second mixing chamber where additional mixing occurs. The thoroughly mixed reactants are discharged into the lower recess 184 from the upper recess 186 through a plurality of apertures 198 (generally, outlets) in the tip 182. The apertures 198 are laterally (radially) offset from the passages 196 in the inner body 174 to promote recirculation and thorough mixing in the second mixing chamber.

A vent passage 200 is also provided in the probe 170. The vent passage 200 extends from an annular cavity 202 formed in the lower face of the outer body 176 to the tubes 152 (FIG. 3) connected to the facility exhaust system (not shown). A series of holes 204 extend through the cover 180 from the annular cavity 202 to an annular recess 206 formed between the tip 182 and a barrier 208 surrounding the tip. The holes 204 permit the reactants and reaction products to pass through the cover 180 and enter the cavity 202 and vent passage 200. The barrier 208 reduces emission of reactants and reaction products beyond the barrier to prevent adjacent substances M on the substrate S from being contaminated. The probe 170 of the second embodiment is identical to the probe 20 of the first embodiment in all other respects.

Figure 6:
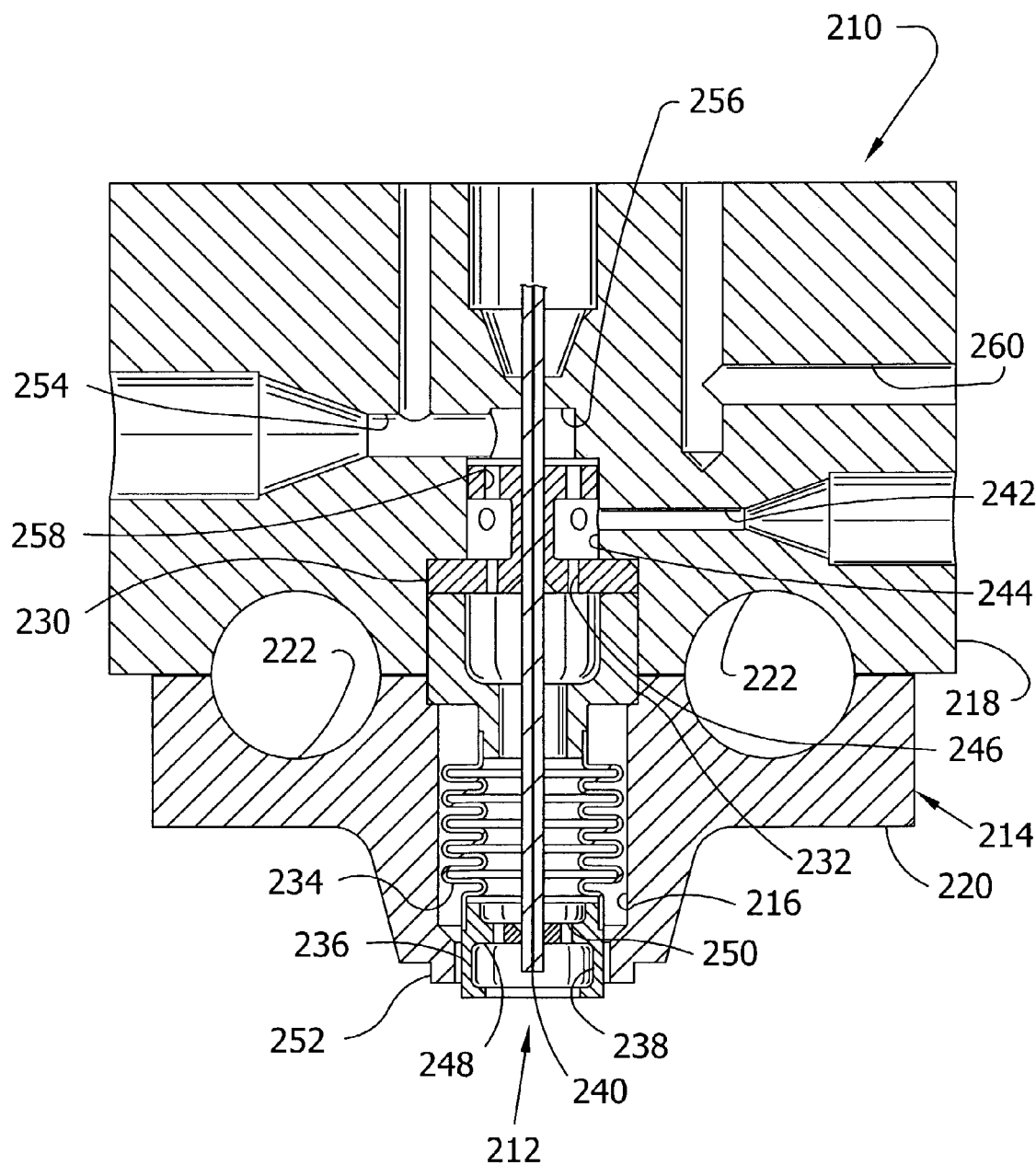
FIG. 6 is a vertical cross section of a third embodiment of the probe of the present invention.

As illustrated in FIG. 6, a probe 210 of a third embodiment includes an inner body, generally designated by 212, and a two-piece outer body, generally designated by 214, having an inner cavity 216 sized and shaped for receiving the inner body. The outer body 214 includes an upper piece 218 and a lower piece 220 attached to the upper piece with screw fasteners (not shown). Grooves 222 are provided in the mating faces of the upper and lower pieces 218, 220 for receiving conventional instrumentation such as heaters (not shown). The inner body 212 includes a spacer 230, an intermediate member 232 positioned below the spacer, a resiliently compliant element 234 attached to the intermediate member, and a cylindrical tip 236 attached to the lower end of the compliant element for engaging the substrate S. The tip 236 has a hollow interior forming a recess 238 sized and shaped for receiving reaction product, and in some embodiments, at least a portion of the substance M when the tip 236 engages the substrate S. Although other compliant elements may be used without departing from the scope the present invention, in one embodiment the compliant element is a bellows.

The upper piece 218 of the outer body 214 includes a product sampling passage 240 extending upward from the recess 238 to the tube 134 (FIG. 3) connected to the product analyzer. The tube 134 transports at least a portion of a reaction product from the product sampling passage 240 to the product analyzer. The upper piece 218 also includes reactant source passages 242 extending through the outer body 214 from tubes 138 (FIG. 3) connected to a plurality of reactant sources (e.g., four separate sources, not shown). The reactant source passages 242 can optionally extend to a mixing chamber 244 defined by a central portion of the spacer 230. The reactant exits the mixing chamber 244 through a plurality of reactant delivery passages 246 in the spacer 230 and then flows through the intermediate member 232 and the resiliently compliant element 234. A wall 248 extending across the tip 236 promotes recirculation and mixing of the reactants inside the bellows prior to entering the recess 238 in the tip 236 through holes 250 (generally, outlets) in the wall. A barrier 252 extends downward from the lower piece 220 of the outer body 214. Preferably, the product sampling passage 240 has a higher resistance to flow than the reactant source passages 242.

An overflow vent passage 254 extends through the outer body 214 from a cavity 256 in the body positioned above the spacer 230. Holes 258 extending through the spacer 230 between the cavity 256 and the mixing chamber 244 permit the reactants to pass through the inner body 212 and enter the overflow vent passage 254. It is envisioned that conventional instrumentation may also be provided in the outer body 214. For example, a hole 260 may be provided in the outer body 214 for receiving a thermocouple for measuring the temperature of the probe 210.

To use the reaction chamber 10 described above, solid and/or liquid substances M are deposited on a substrate S and the substrate is loaded onto the stage 18 in the enclosure 12. The horizontally-oriented actuator assemblies 14 are activated to sequentially align each of the substances M on the substrate S with the probe 20 (or 170 or 210). When one of the substances M is aligned with the probe, the vertically-oriented actuator assembly 16 is activated to lower the probe over the substance. Reactants are injected through the reactant source passages 136 (or 192 or 242) and downward through the corresponding reactant delivery passages 142 (or 196 or 246) in the probe toward the substance to contact the substance. The overflow vent passage 254 allows for higher reactant flow rates with excess reactants being vented through the vent passage 254. Significantly, this approach prevents back diffusion of product gases into the source passage, and allows the contact time (i.e., residence time) to be controlled substantially by the flow rate through the product sampling passage 240 and the recess volume. The reactants are allowed to react in the presence of the substance M on the substrate S to form a reaction product, and at least a portion of the reaction product is withdrawn through the product sampling passage 130 (or 240) to a product analyzer for analysis. In the first and second embodiments, any reactants and/or reaction products which escape from the recess 118 (or 184) are drawn through the holes 154 (or 204) in the cover 120 (or 180) and the vent passage 148 (or 200) to the facility exhaust so they do not contaminate adjacent substances M on the substrate S. Alternatively, the reactants and reaction products can be vented from the recess 238 through the interior of the inner body 212 to the vent passage 254.

Preferably, the probe 20 is used with a plurality of substances deposited in an array on the substrate S, and the steps of delivering, reacting, withdrawing, and analyzing are performed sequentially for each of the substances deposited on the substrate.

Because the inner bodies 102, 212 of the probes 20, 210 of the first and third embodiments include the compressible resilient bellows element 114, 234, the tip 116, 236 can actually contact the substrate S to improve the reaction product sampling. Although the probes 20, 210 may contact the substrate S for other lengths of time without departing from the scope of the present invention, in some preferred embodiments the probes contact the substrate for between about 10 seconds and about 2 minutes. Even though the tip 116 of the first embodiment contacts the substrate S, a perfect seal is not formed between the tip and the substrate on a molecular level. Thus, in embodiments where reactants are delivered to the tip 116 through outlets which are external to the recess 118, at least a portion of the reactants can diffuse under the tip into the recess to react in the presence of the substance M, and reaction products can be withdrawn by the probe 20. The sampling probe 20, 210 contacts the substrate S during at least a portion of the delivering, reacting and withdrawing steps. Preferably, the probe 20, 210 contacts the substrate S during the entire time the reactants are delivered to the recess 118, 238, reacted in the recess and the reaction products are withdrawn from the recess. Although the probe 170 of the second embodiment does not necessarily include a compressible tip, it can be brought very near (e.g., to within about 100 micrometers) the substrate S to improve sampling capability.

Using the touch-down probes 20, 210 of the first and third embodiments, contact times greater than about 1 second (e.g., between about 2 seconds and about 10 seconds) can be achieved. Contact time (i.e., residence time) is a function of reaction cavity volume and reactant flow rate through the cavity and as such, is likewise dependent upon probe design parameters (such as reaction cavity inlet port and outlet port geometries) and process conditions (such as fluid pressures). The residence time is equal to the reaction cavity volume divided by the reactant flow rate through the cavity. Using the probes 20, 210 of the first and third embodiments, improved contact times can be achieved, and extremely small quantities of reaction products from low activity reactants can be detected. Although the recess 118 may have other volumes without departing from the scope of the present invention, the recess of one preferred embodiment has a volume of about 10 microliters. Although the product sampling passages 130 may have other flow rates without departing from the scope of the present invention, the flow rate of the product sampling passage of one preferred embodiment is between about 1 and about 10 microliters per second. Thus, the probe 20 of one preferred embodiment has a contact time of between about 1 second and about 10 seconds.

Although the probes 20, 210 of the first and third embodiment are described as contacting the substrate S, a perfect seal is not created on a molecular level. It is envisioned that the tip 116, 236 of the probes 20, 210 can be treated with a compressibly resilient material (e.g., a synthetic rubber, quartz fiber or graphite diffusion gasket) to improve sealing capability. Alternatively, it is envisioned that the tip 116, 236 may include grooves 262 (FIG. 4) or other openings to increase flow under and through the tip.

Although the probes of the present invention are described as being used in combination with a scanning mass spectrometer, those skilled in the art will appreciate that the probe may be used with other reaction product analyzers. For example, it is envisioned that the probes of the present invention may be used in combination with a photothermal deflection spectrometer as described in U.S. Pat. No. 6,087,181.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A method for sampling reaction products, said method comprising the steps of:
   delivering a reactant through a sampling probe to contact a substance deposited on a substrate;
   allowing the reactant to react with the substance to form a reaction product;
   withdrawing at least a portion of the reaction product through the sampling probe;
   contacting the sampling probe with the substrate during at least a portion of the delivering, allowing and withdrawing steps so that a tip of the sampling probe may tilt to engage the substrate entirely around the substance; and
   analyzing, the withdrawn portion of the reaction product.

2. A method as set forth in claim 1 wherein the contacting step includes tilting a tip of the sampling probe so that the tip of the probe engages the substrate entirely around the substance.

3. A method as set forth in claim 1 wherein the probe is contacted with the substrate for less than about 2 minutes during the delivering, allowing and withdrawing steps.

4. A method as set forth in claim 3 wherein said substance is a first substance of a plurality of substances deposited in an array on the substrate, and the steps of delivering, allowing, withdrawing, contacting and analyzing are performed sequentially for each of the substances deposited on the substrate.

5. A method as set forth in claim 1 wherein the reactant has a contact time with the substance of greater than about 1 second.

6. A method as set forth in claim 1 wherein the reactant has a contact time with the substance of between about 2 seconds and about 10 seconds.

7. A method as set forth in claim 1 further comprising the step of venting excess reaction product through the sampling probe.

* * * * *